United States Patent [19]

Bowman

[11] 4,226,795

[45] Oct. 7, 1980

[54] PURGE GAS IN METHANOL SYNTHESIS

[75] Inventor: Edward B. Bowman, Beaumont, Tex.

[73] Assignee: E. I. Du Pont de Nemours and Company, Wilmington, Del.

[21] Appl. No.: 36,242

[22] Filed: May 4, 1979

Related U.S. Application Data

[63] Continuation-in-part of Ser. No. 882,917, Mar. 2, 1978, abandoned.

[51] Int. Cl.² .............................................. C07C 31/06
[52] U.S. Cl. .................................................. 210/449.5
[58] Field of Search ...................................... 260/449.5

[56] References Cited

U.S. PATENT DOCUMENTS

| | | | |
|---|---|---|---|
| 3,064,029 | 11/1962 | White ................................. | 260/449.5 |
| 3,186,145 | 6/1965 | Pelton et al. ....................... | 260/449.5 |
| 3,254,967 | 6/1966 | Wentworth .................... | 260/449.5 X |
| 3,615,200 | 10/1971 | Konoki .............................. | 260/449.5 |
| 3,940,428 | 2/1976 | Connell et al. .................... | 260/449.5 |

FOREIGN PATENT DOCUMENTS

| | | | |
|---|---|---|---|
| 836909 | 6/1960 | United Kingdom ................. | 260/449.5 |
| 1159035 | 7/1969 | United Kingdom ................. | 260/449.5 |
| 1259945 | 1/1972 | United Kingdom ................. | 260/449.5 |
| 1484366 | 9/1977 | United Kingdom ................. | 260/449.5 |

*Primary Examiner*—Howard T. Mars

[57] ABSTRACT

Utilization of hydrocarbon feedstocks in the manufacture of methanol by catalytic conversion of synthesis gas is improved by adding a carbon oxide to a hydrogen-rich purge gas from the process and catalytically converting the carbon oxide-enriched purge gas in a secondary reactor to form additional methanol. The secondary reactor effluent consists essentially of methanol, water and unreacted gases. Methanol is readily separated therefrom.

23 Claims, 2 Drawing Figures

PURGE GAS IN METHANOL SYNTHESIS

CROSS-REFERENCE TO RELATED APPLICATIONS

The application is a continuation-in-part of copending application Ser. No. 882,917, filed Mar. 2, 1978 now abandoned.

DESCRIPTION

1. Technical Field

The invention relates to the manufacture of methanol and more particularly to such manufacture from synthesis gas and the utilization of purge gas therefrom.

2. Background Art

Methanol is one of the important basic chemical commodities in the modern world. It is used as an ingredient of automotive and other antifreezes. It is also used as a constituent of solvent systems for many processes and is a basic raw material for the manufacture of formaldehyde. Methanol is also used in the manufacture of many methyl esters, methyl halides, methyl ethers, methyl amines, methacrylates, dimethyl terephthalate and ethylene glycol.

Though methanol can be made by a number of different processes such as sponification of methyl chloride, low pressure hydrogenation of carbon monoxide and Fischer-Tropsch synthesis, by far the most widely used route to methanol is by catalytic conversion of synthesis gas derived from hydrocarbons such as coal, coke, petroleum residues and light hydrocarbon-containing streams, especially natural gas.

In a typical process, desulfurized natural gas is steam reformed at an elevated pressure over a nickel catalyst to form a synthesis gas comprising $H_2$ and CO in a molar ratio of about 2:1. To promote the water-gas shift reaction, carbon dioxide is frequently mixed with the natural gas and steam prior to reforming. For example, in U.S. Pat. No. 3,943,236 to R. V. Green, a portion of the reformer effluent from which the CO has been removed is admixed with $CO_2$ in an amount at least equivalent to the amount of $H_2$ present and recycled to the reformer inlet. U.S. Pat. No. 3,763,205 to R. V. Green describes a methanol synthesis process from the aforesaid steam reformed synthesis gas. In this process, the synthesis gas is compressed to 137-409 atmospheres (2000-6000 psig) and mixed with high pressure hydrogen-rich recycle gas. The mixture is passed through a fixed bed reactor, normally containing a metal oxide catalyst such as zinc, zinc-chromium, chromium-copper or copper. The methanol reactor (converter) usually operates at temperatures of about 285° to 400° C. The hot reactor effluent is cooled by heat exchange with incoming feed and with water to generate steam. The cooled reactor effluent is then passed to one or more separators in which the normally gaseous effluent materials are separated from the normally liquid materials. At least the high pressure component of the effluent gas, which contains mainly hydrogen, is recycled to the inlet of the methanol converter where, as indicated above, it is mixed with incoming synthesis gas and fed to the fixed-bed reactor.

A particularly preferred reactor for methanol synthesis is the so-called "cold shot reactor" disclosed in U.S. Pat. No. 3,254,967 to T. O. Wentworth. In this reactor, "cold" hydrogen gas is introduced between each of a plurality of fixed catalyst beds to obtain more thorough mixing and better temperature control.

Reactor effluent vapor, which contains mainly methanol, hydrogen, methane, water, CO, $CO_2$ and $N_2$ is passed through a series of indirect heat exchangers to effect cooling to 30° to 50° C.

Another illustrative high pressure process is described in U.S. Pat. No. 3,501,516 to R. W. Parrish (34-680 atmospheres, 500-10,000 psia) where purge gas is removed so that the remainder of the residual gas, which is recycled to the converter feed, has its composition maintained at a desired level.

In addition to high pressure methanol synthesis processes, there are also low pressure processes, i.e., pressures below 150 atmospheres. Illustrative processes are described in British Pat. Nos. 1,190,071; 1,259,945 and 1,484,366. In addition, in 1,190,071, the hydrocarbon content of the purge gas is utilized to generate additional hydrogen and carbon oxides. In U.S. Pat. No. 1,259,945, the purge gas is compressed and fed to an additional methanol synthesis stage where further methanol is produced despite the increased inert concentration. A similar process is described in U.S. Pat. No. 3,615,200, issued to K. Konoki.

Heretofore, it has usually been customary to use methanol synthesis loop purge gas as fuel. However, this is now uneconomical due to the increased costs of hydrocarbon feedstocks such as natural gas. While the aforesaid British Pat. Nos. 1,190,071 and 1,259,945 and U.S. Pat. No. 3,615,200 do utilize purge gas, the process of the present invention is directed to the utilization of the methanol reactant values and energy of the purge gas while minimizing the effects of inerts contained therein.

DISCLOSURE OF THE INVENTION

According to the present invention, there is provided a process for the manufacture of methanol using a hydrogen-containing gaseous purge stream from a chemical manufacturing process comprising:

(a) raising the pressure of a second hydrogen-containing gaseous stream at a lower pressure than the purge stream by combining the two streams and feeding the combined streams to a hydrogen-enrichment zone;

(b) raising the hydrogen concentration in the combined stream in the hydrogen-enrichment zone by removing gaseous materials therefrom which are inert with respect to a methanol synthesis reaction;

(c) adjusting the hydrogen to carbon oxide molar ratio of the hydrogen-enriched gas stream to a level within the range of about 2:1 to 12:1 by addition of carbon oxide thereto;

(d) feeding the carbon oxide-adjusted hydrogen-enriched gas stream to a methanol synthesis zone containing a methanol synthesis catalyst and forming a methanol-containing gaseous effluent, said zone maintained at a temperature below which any substantial methanation occurs and at a pressure no higher than the pressure of the purge stream; and (e) recovering methanol from the gaseous effluent.

According to the preferred embodiment, there is provided a process for the manufacture of methanol by (1) catalytic conversion of synthesis gas in a primary methanol synthesis zone to form an effluent comprising a mixture of crude methanol, hydrogen, methane, water, carbon monoxide, carbon dioxide and nitrogen; (2) separation of crude methanol and water from the effluent to form a hydrogen-rich gas stream containing carbon oxides and materials which are inert with respect to the methanol convertion reaction; (3) recycling the hydrogen-rich gas stream to the inlet of the primary synthesis zone by which the level of inert gases in the hydrogen-rich gas stream therefrom is increased and (4) purging a portion of the hydrogen-rich gas stream from the process cycle to maintain the inert gas level in the recycled hydrogen-rich gas stream below preselected maximum limits, the improvement comprising:

(a) raising the pressure of a second hydrogen-containing gaseous stream at a lower pressure than the purge stream by combining the two streams and feeding the combined streams to a hydrogen-enrichment zone;

(b) raising the hydrogen concentration of the combined stream by removing inert gaseous materials therefrom in the hydrogen-enrichment zone;

(c) adjusting the hydrogen to carbon oxide molar ratio of the hydrogen-enriched purge gas stream from which inert gases have been removed to a level of between about 2:1 and about 12:1 by addition of a carbon oxide thereto;

(d) catalytically converting the carbon oxide-adjusted hydrogen-enriched gas stream in a secondary methanol synthesis zone at a pressure no higher than the pressure in the primary synthesis zone to form an effluent comprising a mixture of methanol, water and unreacted gases;

(e) maintaining the temperature within the secondary synthesis zone at a level below which any substantial methanation occurs by indirect transfer of heat from the secondary synthesis zone effluent to the carbon oxide-adjusted hydrogen-enriched gaseous feed thereto; and (f) separating methanol and water from the secondary synthesis zone effluent.

BEST MODE INCLUDING EXAMPLES

Figure 1:
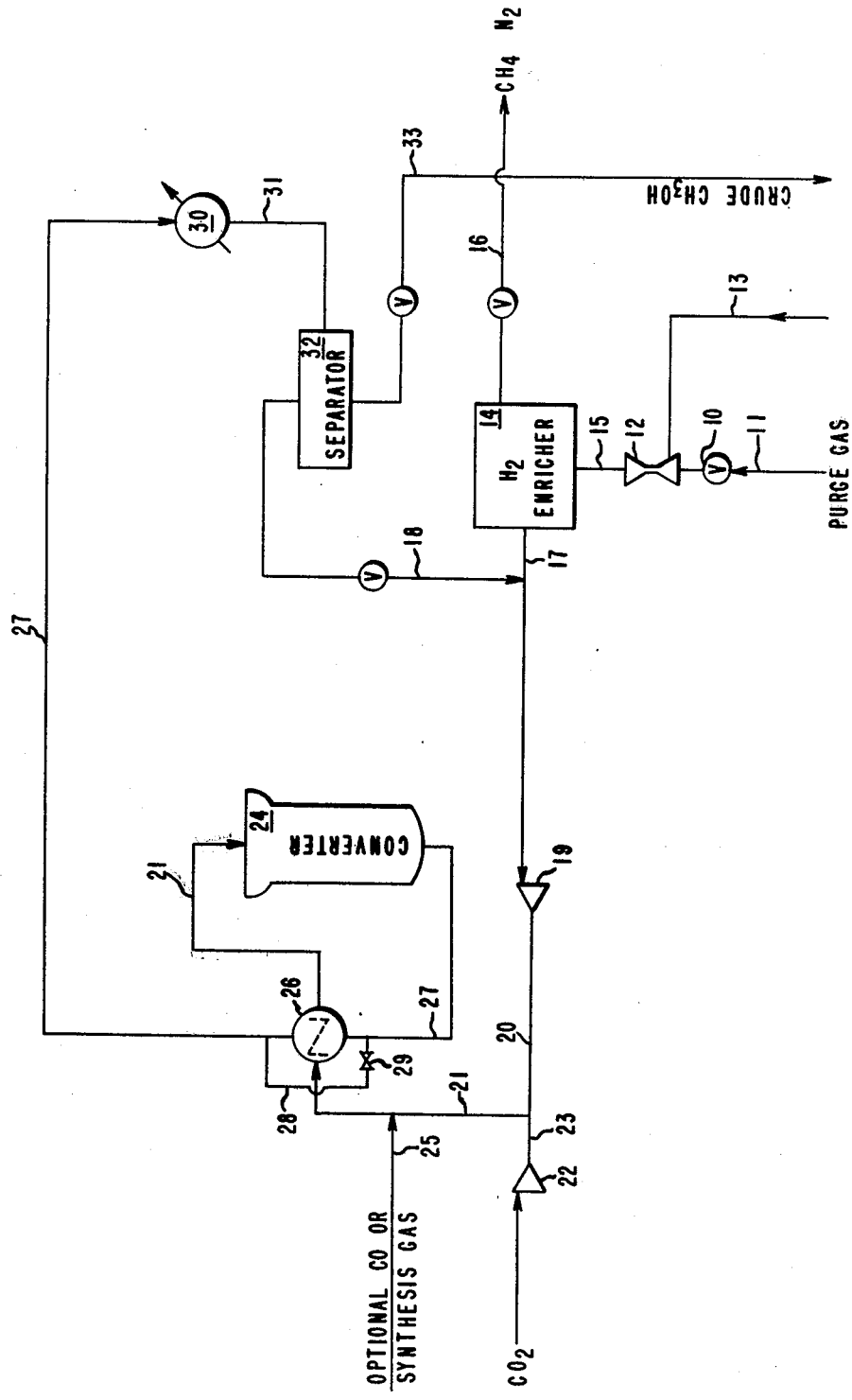
FIG. 1 is an illustrative flow diagram showing the manufacture of methanol using a hydrogen-containing gas stream which is a purge stream from a chemical manufacturing process such as a methanol process or an ammonia process.

Referring to FIG. 1, a hydrogen-containing purge stream from a chemical manufacturing process, such as a methanol synthesis process, an ammonia synthesis process or a process for the reduction of nitrobenzene with hydrogen, is passed through valve 10 in line 11 to jet compressor 12 where the energy of the purge gas is used to compress another hydrogen-containing purge stream at a lower pressure in line 13 to some intermediate level. The combined, compressed gas stream is fed to hydrogen enricher 14 through line 15. In the hydrogen enricher, gaseous materials which are inert with respect to a methanol synthesis reaction are removed from the purge gas, such as by use of a permeator, absorption, adsorption, or through cryogenics, to raise the hydrogen concentration therein. The removed inert gases (predominantly methane for a methanol purge gas and methane and nitrogen for an ammonia purge gas) leave enricher 14 through line 16 for burning or for recycling to a synthesis gas reformer.

Hydrogen enrichment by absorption is described in U.S. Pat. No. 3,064,029, issued to T. C. White on Nov. 13, 1962. Methane can be removed from a gas mixture by absorption as described in U.S. Pat. No. 2,820,071, issued Jan. 14, 1958 to N. H. Ceaglske. A preferred method of hydrogen enrichment is pressure swing adsorption (PSA) such as described by H. A. Steward and J. L. Heck, "Hydrogen Purification by Pressure Swing Adsorption," Chemical Engineering Progress, p. 78, September, 1969. Hydrogen enrichment by cryogenics is described by Wolfgang Förg, "Purification of Hydrogen by Means of Low Temperatures," Linde Reports on Science and Technology, 15/1970. Hydrogen enrichment by the use of permeators is described by R. I. Gardner et al., "Hollow Fiber Permeators for Separating Gases," Chemical Engineering Progress, Vol. 73, No. 1, pp. 76–78, October, 1977.

The hydrogen-enriched gas stream leaves the hydrogen enricher through line 17 where it is then joined in a preferred embodiment with gaseous effluent in line 18 which is being recycled from a methanol converter. The hydrogen-enriched gas stream as it leaves the enricher is predominantly hydrogen with minor amounts of other gases such as $CO_x$ and nitrogen. This gas stream will generally have a composition on a molar basis of about 70–100% hydrogen and up to about 30% of $CO_x$ with minor amounts of other gases. As would be expected, the composition will be dependent upon the route taken for hydrogen enrichment and the source of the purge gas.

The hydrogen-enriched gas stream is compressed by compressor 19, if needed, passes through line 20 and is then joined in converter feed line 21 with carbon dioxide which is fed through compressor 22 and line 23. Carbon dioxide is used to adjust the hydrogen to carbon oxide molar ratio of the gaseous feed to methanol converter 24 to a level in the range of about 2:1 to 12:1, preferably about 2:1 to 8:1, along with optional carbon monoxide which is fed into the carbon-adjusted hydrogen-enriched gas stream in line 21 by line 25. The optional carbon monoxide is used to optimize conversion and to supplement the carbon monoxide in recycle stream 18 to aid in temperature control of converter 24 and affect a lower byproduct water concentration in crude methanol (line 33).

The hydrogen to carbon oxide molar ratio as used herein is defined as $H_2-CO_2/CO+CO_2=2:1$ to $12:1$. In general the converter feed in line 21 is predominantly hydrogen which contains about 2–8 mole percent carbon monoxide, about 3–28 mole percent carbon dioxide and less than 3.5 mole percent of methane, nitrogen and other inert gases.

The carbon oxide-adjusted hydrogen-enriched converter feed stream 21 is passed to converter 24 through a heat exchanger 26, which may be integral with 24, where the feed is preheated to reaction temperature by transfer of heat with the methanol-containing gaseous effluent in line 27 from converter 24. A particularly useful converter is described in British Pat. No. 1,389,709. Feed temperature is controlled to maximize methanol manufacture and to keep it to a level below which any substantial methanation occurs by varying the amount of heat transfer in exchanger 26 with a bypass line 28 controlled by valve 29. Temperature control is also accomplished by adjusting the carbon dioxide to carbon monoxide ratio in the feed stream to take advantage of the lower heat evolution of the carbon dioxide to methanol reaction ($CO_2+3H_2\rightarrow CH_3OH+$-

H₂O) versus the carbon monoxide to methanol reaction ($CO + 2H_2 \rightarrow CH_3OH$). Temperature at which methanation becomes significant is dependent upon pressure and catalyst; however, the methanol synthesis temperature will generally be in the range of about 200° to 400° C., and preferably will be about 250° to 350° C. for converters other than isothermal. For an isothermal converter, the upper reaction temperature is about 300° C.

Pressure in converter 24 will generally be in the range of about 40–155 atm (about 600–2250 psig), preferably about 45–155 atm (about 700–2250 psig). The pressure ranges in atmospheres as used herein are only approximate values with respect to pressure values in pounds per square inch gauge (psig).

The methanol synthesis catalyst contained in converter 24 can be any of those known in the art which are operable under specific converter pressures. Typically, methanol synthesis catalysts are copper-containing. Examples of useful catalyst compositions (reduced form) and their typical temperatures and pressures of operation are as follows:

| Catalyst | Pressure-Atm (psig) | Temperature (°C.) |
|---|---|---|
| $Cu/ZnO/Al_2O_3$ | 273 (4000) | 270 |
| $ZnO/Cr_2O_3$ | 273–341 (4000–5000) | 350–400 |
| Cu/ZnO/V oxides[1] | 44 (630) | 230 |
| $Cu/ZnO/Al_2O_3$[2] | 51 (735) | 250 |
| $Cu/ZnO/Cr_2O_3$[3] | 103 (1500) | 260 |
| Cu/ZnO/mixture of rare earth oxides[4] | 53 (770) | 270 |
| $Cu/ZnO/Cr_2O_3$[5] and a $Cu/ZnO/Al_2O_3$ + B[6] | 130 (1900) | 240 |

[1] U.S. Pat. No. 3,897,471
[2] U.S. Pat. Nos. 3,923,694 and 3,850,850
[3] Canadian Patent 925,069
[4] U.K. Patent 1,364,096
[5] U.S. Pat. No. 3,840,478
[6] German Patent 2,449,493

The gaseous effluent from converter 24 is passed through condenser 30 and then via line 31 to methanol recovery. Separator 32 operating at a pressure of 600–2000 psig (about 40–135 atm) separates methanol and water (with dissolved hydrogen and $CO_x$ therein) from unreacted and inert gases and sends this crude methanol through line 33 to further separation and a conventional methanol refining unit. The energy is streams 33 and 18 may be reclaimed by using expanders in place of valves if economically justified. The off-gas in line 18 from separator 32 is basically hydrogen, $CO_x$ and a little (less than 5 mole percent) nitrogen. It is preferred to recycle the off-gas to the hydrogen-enriched gas stream via line 18 in order to recover the carbon oxide values therein (about 25 mole percent); however, alternatively, the gas can be burned or, if hydrogen enrichment occurs via a permeator where carbon monoxide is passed through, secondary synthesis may not need a recycle of unreacted gases. In this latter case, unreacted gases would be recovered via lines 33 and 13.

Figure 2:
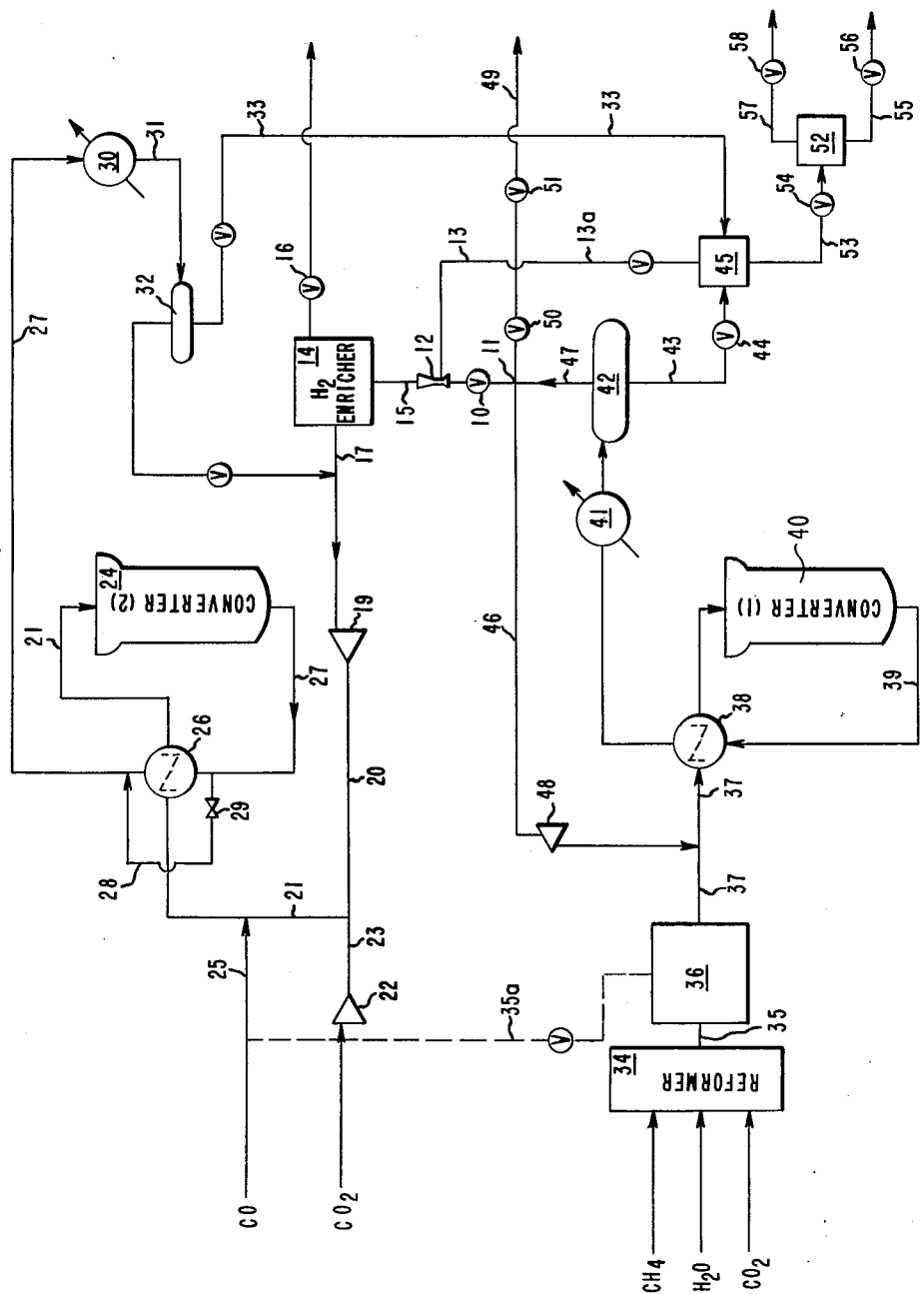
FIG. 2 is an illustrative flow diagram showing a preferred embodiment for the manufacture of methanol using a hydrogen-containing purge stream from a high pressure methanol synthesis process.

In a preferred embodiment as illustrated in FIG. 2, the hydrogen-containing purge gas in line 11 fed through jet compressor 12 to hydrogen enricher 14 is derived from a primary methanol synthesis process, preferably one operated at high pressure, i.e., about 1000–5000 pounds per square inch guage, (about 70–340 atm) and preferably about 4000–5000 pounds per square inch gauge (about 270–340 atm), so that the energy of the purge stream can be used to compress hydrogen-containing purge stream 13 which is at a lower pressure, e.g., about 100–2000 pounds per square inch guage (about 8–135 atm), and preferably 100–600 pounds per square inch gauge (about 8–40 atm). While high pressure synthesis processes are preferred, lower pressure processes, i.e., about 600–750 psig (about 40–50 atm), can also be used. In this case, purge stream 13 is at a lower pressure, e.g., about 50 psig (4.5 atm), and supplemental pressure has to be used to get converter 24 up to a useful pressure.

A methanol synthesis process normally includes, in addition to the synthesis section, a synthesis gas generating section in which a carbonaceous feedstock is converted to carbon oxides and hydrogen by a high temperature reaction with steam, optionally with carbon dioxide such as described in U.S. Pat. No. 3,943,236. This synthesis process has many forms which are well known and the process used will depend upon the carbonaceous feedstock used.

In the present process, it is preferred to start with natural gas and generate synthesis gas by "steam reforming" in reformer section 34. The exiting gas in line 35 is at a pressure typically up to about 20 atmospheres absolute and usually has to be compressed before feeding it to the methanol synthesis. Thus, the synthesis gas in line 35 is compressed by compressor 36 and is fed through heat exchanger 38 via line 37 where the gas is preheated to reaction temperature by heat transfer with the methanol-containing effluent in line 39 from the primary methanol converter 40. The construction of converter 40 and the catalyst contained therein can be any of those described in the art and can be the same as or different from secondary converter 24. Typical catalysts were mentioned previously. The reaction temperature in converter 40 depends upon the catalyst used and operating pressure. At low pressure, i.e., about 1000 psig (70 atm), the temperature will usually be about 250°–350° C., whereas at the higher end of the pressure range, i.e., about 4000–5000 psig (270–340 atm), the temperature will usually be about 350° to 400° C.

A portion of the synthesis gas can also be used as a source of carbon monoxide which can be used to adjust the carbon dioxide to carbon monoxide and hydrogen to carbon ratios in the feed to the secondary converter. Thus, synthesis gas can be passed through optional valved line 35a to secondary converter feed in line 21.

The methanol-containing gaseous effluent (also containing the unreacted gases hydrogen and carbon oxides, water, and gases inert to the methanol reaction, i.e., methane, nitrogen and minor amounts of other materials) from converter 40 is passed through condenser 41 and then to methanol recovery and purge gas utilization.

Condensed effluent is separated from gaseous effluent in high pressure separator 42 operating at essentially the same pressure as converter 40. Crude methanol and water with unreacted gases dissolved therein is passed via line 43 and valve 44 to intermediate pressure separator 45 operating at about 100–600 psig (about 8–40 atm) and normally about 300 psig (about 20 atm), wherein a portion of the dissolved gases is released. The hydrogen-containing high pressure gas stream from separator 42 is primarily recycled via lines 46 and 47 and recycle compressor 48 (if necessary) to the feed to primary converter 40.

As practiced heretofore, when the level of inert gases in the recycle gas reaches a predetermined maximum level, a purge of the gas is taken via line 49 and valves 50 and 51 which is then burned. In the present process, this purge stream for burning approaches zero due to the fact that it now is used to produce additional methanol in a process as shown in FIG. 1.

The hydrogen-containing off-gas from intermediate pressure separator 45 passes via line 13 and 13a to jet compressor 12 where it is compressed by the energy from the hydrogen-containing purge gas from high pressure separator 42. In the preferred embodiment, separator 45 is also used to receive the crude methanol with unreacted gases dissolved therein produced by the secondary converter 24. This crude methanol in line 33 is from higher pressure separator 32 as described previously.

Methanol and water with remaining unreacted gases dissolved therein is passed from separator 45 to low pressure separator 52 via line 53 and valve 54. This separator is only slightly above atmospheric pressure. Crude methanol is passed through line 55 and valve 56 to a conventional methanol refining unit. The remaining unreacted and inert gases along with any low-boiling impurities are passed through line 57 and valve 58 for burning.

The present invention has the advantage of preparing additional methanol from hydrogen-containing purge streams which have previously been burned. Energy utilization is high because (1) the methane separated from the hydrogen enricher will yield about 70% of the heating value now derived from burning the hydrogen-containing purge stream, and (2) energy in the form of pressure in the purge stream is used to compress a lower pressure purge stream.

The invention can be further understood by the following example in which parts and percentages are on a molar basis unless otherwise indicated.

EXAMPLE

A methanol synthesis process based on the supply of purge gas from a high pressure methanol synthesis process is illustrated. The compositions, flow rates, pressures and temperatures of the process effluents are set forth in Table I with line references to FIG. 1 and FIG. 2.

The primary reactor used is of the cold shot type similar to that described in U.S. Pat. No. 3,254,967 and the secondary reactor is a tubular isothermal reactor similar to that described in U.K. Pat. No. 1,389,709. The catalyst in the primary reactor is zinc chromite ($ZnO/Cr_2O_3$) and the catalyst in the secondary reactor is Cu/ZnO/V oxides.

Hydrogen enrichment is conducted by pressure swing adsorption such as described in H. A. Stewart and J. L. Heck, "Hydrogen Purification by Pressure Swing Adsorption," Chemical Engineering Progress, p. 78, September, 1969.

TABLE I

| | Line | Press. (Atm) | Temp. (°C.) | Composition (Mole %) | | | | | | | | Flow Rate (lb/hr) |
|---|---|---|---|---|---|---|---|---|---|---|---|---|
| | | | | $H_2$ | CO | $CO_2$ | $CH_4$ | $N_2$ | $H_2O$ | $CH_3OH$ | Other | |
| 11 | H.P. Purge | 305 | 40 | 73.6 | 5.3 | 1.9 | 17.1 | 1.7 | 0.1 | 0.2 | 0.1 | 6,322 |
| 13 | L.P. Purge | 19 | 40 | 47.1 | 2.8 | 10.1 | 35.8 | 2.2 | 0.2 | 1.6 | 0.2 | 9,666 |
| 15 | $H_2$ Enricher Feed | 43 | 40 | 61.6 | 4.2 | 5.6 | 25.6 | 1.9 | 0.1 | 0.8 | 0.1 | 15,988 |
| 16 | Inerts-Fuel | 0.7 | 32 | 18.1 | 6.4 | 13.2 | 60.2 | 2.2 | — | — | — | 12,545 |
| 17 | $H_2$-rich Stream | 40 | 46 | 95.6 | 2.6 | — | — | 1.8 | — | — | — | 2,891 |
| 20 | $H_2$-rich + Recycle | 135 | 54 | 87.1 | 3.5 | 8.3 | — | 1.1 | — | — | — | 10,051 |
| 23 | $CO_2$ Feed | 135 | 54 | — | — | 100 | — | — | — | — | — | 15,954 |
| 21 | Conv. Feed | 135 | 200 | 70.1 | 2.8 | 26.2 | — | 0.9 | — | — | — | 26,005 |
| 27 | Conv. Efflu. | 125 | 265 | 39.3 | 4.4 | 16.6 | — | 1.2 | 19.5 | 19 | — | 26,005 |
| 13a | L.P. Purge | 19 | 40 | 49 | 2.9 | 10.4 | 33.3 | 2.3 | 0.2 | 1.6 | 0.3 | 11,738 |
| 18 | Recycle | 40 | 40 | 73.9 | 4.9 | 21.2 | — | (1) | — | — | — | 7,160 |
| 33 | Crude $CH_3OH^{(2)}$ | 19 | 40 | 12.6 | 3.9 | 13.1 | — | 2.2 | 34.5 | 33.7 | — | 18,842.5 |
| 43 | Crude $CH_3OH^{(1)}$ | 19 | 40 | 3.6 | 0.2 | 1.1 | 3.1 | 0.2 | 27.3 | 64.0 | 0.5 | 265,522 |
| 53 | Crude $CH_3OH$ to L.P. Sep. | 19 | 40 | 0.15 | 0.26 | 1.19 | 0.04 | 0.13 | 30.38 | 67.36 | 0.49 | 272,627 |
| 49 | Excess Purge to Fuel | 19 | 40 | 56.9 | 3.4 | 12.1 | 22.4 | 2.9 | 0.2 | 1.8 | 0.3 | 2,072 |

$^{(1)}$up to $\cong$ 2.0% $N_2$.

I claim:

1. A process for the manufacture of methanol using a hydrogen-containing gaseous purge stream from a chemical manufacturing process comprising:
   (a) raising the pressure of a second hydrogen-containing gaseous stream at a lower pressure than the purge stream by combining the two streams and feeding the combined streams to a hydrogen-enrichment zone;
   (b) raising the hydrogen concentration in the combined stream in the hydrogen-enrichment zone by removing gaseous materials therefrom which are inert with respect to a methanol synthesis reaction;
   (c) adjusting the hydrogen to carbon oxide molar ratio of the hydrogen-enriched gas stream to a level within the range of about 2:1 to 12:1 by addition of a carbon oxide thereto;

(d) feeding the carbon oxide-adjusted hydrogen-enriched gas stream to a methanol synthesis zone containing a methanol synthesis catalyst and forming a methanol-containing gaseous effluent, said zone maintained at a temperature below which any substantial methanation occurs and at a pressure no higher than the pressure of the purge stream; and (e) recovering methanol from the gaseous effluent.

2. The process of claim 1 wherein the hydrogen to carbon oxide ratio is adjusted to a level in the range of about 2:1 to 8:1 by adding at least one of carbon dioxide and carbon monoxide.

3. The process of claim 2 wherein the methanol synthesis zone is maintained at a temperature in the range of about 200° to 400° C. and a pressure in the range of about 40–155 atmospheres.

4. The process of claim 3 wherein the gaseous effluent is cooled, methanol and water separated therefrom and a portion of the resulting gaseous effluent recycled to the hydrogen-enriched gas stream.

5. The process of claim 4 wherein the portion recycled is about 10–80 mole percent of the gaseous effluent.

6. The process of claim 3 wherein the hydrogen to carbon oxide ratio is adjusted by injecting carbon dioxide into the hydrogen-enriched gas stream and by recycling a portion of the gaseous effluent which contains unreacted carbon dioxide and carbon monoxide, said stream being predominantly hydrogen which contains about 2–8 mole percent carbon monoxide, about 3–28 mole percent carbon dioxide, and less than 3.5 mole percent of gases inert to a methanol synthesis reaction.

7. The process of claim 3 wherein the temperature of the synthesis zone is maintained by heat transfer between the gaseous effluent and the carbon oxide-adjusted hydrogen-enriched gas stream fed to the methanol synthesis zone.

8. The process of claim 1 wherein hydrogen-containing purge stream is from a methanol synthesis process or from an ammonia synthesis process.

9. The process of claim 2 wherein the methanol synthesis zone is maintained at a temperature in the range of about 250° to 350° C. and a pressure in the range of about 45–155 atmospheres; and the hydrogen-containing purge stream is at a pressure in the range of about 270–340 atmospheres and the second hydrogen-containing stream is a hydrogen and carbon oxide-containing gas stream.

10. In a process for the manufacture of methanol by (1) catalytic conversion of synthesis gas in a primary methanol synthesis zone to form an effluent comprising a mixture of crude methanol, hydrogen, methane, water, carbon monoxide, carbon dioxide and nitrogen; (2) separation of crude methanol and water from the effluent to form a hydrogen-rich gas stream containing carbon oxides and materials which are inert with respect to the methanol conversion reaction; (3) recycling the hydrogen-rich gas stream to the inlet of the primary synthesis zone by which the level of inert gases in the hydrogen-rich gas stream therefrom is increased and (4) purging a portion of the hydrogen-rich gas stream from the process cycle to maintain the inert gas level in the recycled hydrogen-rich gas stream below preselected maximum limits, the improvement comprising:

(a) raising the pressure of a second hydrogen-containing gaseous stream at a lower pressure than the purge stream by combining the two streams and feeding the combined streams to a hydrogen-enrichment zone;

(b) raising the hydrogen concentration of the combined stream by removing inert gaseous materials therefrom in the hydrogen-enrichment zone;

(c) adjusting the hydrogen to carbon oxide molar ratio of the hydrogen-enriched gas stream from which inert gases have been removed to a level of between about 2:1 and about 12:1 by addition of a carbon oxide thereto;

(d) catalytically converting the carbon oxide-adjusted hydrogen-enriched gas stream in a secondary methanol synthesis zone at a pressure no higher than the pressure in the primary synthesis zone to form an effluent comprising a mixture of methanol, water and unreacted gases;

(e) maintaining the temperature within the secondary synthesis zone at a level below which any substantial methanation occurs by indirect transfer of heat from the secondary synthesis zone effluent to the carbon oxide-adjusted hydrogen-enriched gaseous feed thereto; and (f) separating methanol and water from the secondary synthesis zone effluent.

11. The process of claim 10 wherein secondary synthesis zone effluent is admixed with primary synthesis zone effluent prior to separation of methanol and water therefrom.

12. The process of claim 11 wherein the secondary synthesis zone effluent is cooled, methanol and water separated therefrom and a portion of unreacted gases from the effluent admixed with the primary synthesis zone effluent.

13. The process of claim 12 wherein the gaseous portion admixed with primary synthesis zone effluent is about 20–90 mole percent of unreacted gases from the secondary synthesis zone effluent.

14. The process of claim 13 wherein the gaseous portion admixed with primary synthesis zone effluent is that which is dissolved in the methanol and water separated from the secondary synthesis zone effluent and the remaining unreacted gases are recycled to the hydrogen-enriched gas stream.

15. The process of claim 10 wherein the carbon oxide added in step (c) is at least one of carbon dioxide and carbon monoxide.

16. The process of claim 10 wherein the temperature is maintained in step (e) by also adjusting the molar ratio of carbon dioxide to carbon monoxide in the feed to the secondary synthesis zone while maintaining the hydrogen to carbon oxide molar ratio within the range of about 2:1–12:1.

17. The process of claim 15 wherein the carbon oxide added in step (c) is carbon dioxide, or a carbon dioxide-containing stream.

18. The process of claim 15 wherein the carbon oxide added in step (c) is carbon monoxide from a source outside the methanol synthesis process or carbon monoxide from synthesis gas generation.

19. The process of claim 10 wherein the catalyic conversion of step (d) is conducted in the presence of a copper-containing catalyst at a temperature in the range of about 200° to 400° C. and a pressure in the range of about 40–155 atmospheres.

20. The process of claim 19 wherein the temperature is in the range of about 250° to 350° C. and the pressure is in the range of about 45–155 atmospheres.

21. The process of claim 20 wherein the step (d) pressure is lower than the pressure in the primary synthesis zone.

22. The process of claim 14 wherein (1) the separated methanol and water from the secondary synthesis zone, with gases dissolved therein, is admixed with separated methanol and water from the primary synthesis zone, with gases dissolved therein; (2) the pressure of the admixture is reduced to a level sufficient to release the dissolved gases; (3) the released gases comprise the second hydrogen-rich gas stream compressed by and combined with the purge stream.

23. The process of claim 22 wherein the released gases are at a pressure in the range of about 8–40 atmospheres and hydrogen-rich purge gas stream is at a pressure in the range of about 240–340 atmospheres.

* * * * *